United States Patent
Łojkowski et al.

(10) Patent No.: US 9,675,459 B2
(45) Date of Patent: Jun. 13, 2017

(54) METHOD FOR MANUFACTURING BONE IMPLANTS AND BONE IMPLANT

(71) Applicant: INSTYTUT WYSOKICH CIŚNIEŃ POLSKIEJ AKADEMII NAUK, Warsaw (PL)

(72) Inventors: Witol Łojkowski, Warsaw (PL); Tadeusz Chudoba, Warsaw (PL); Elżbieta Pietrzykowska, Łochów (PL); Aleksandra Kędzierska, Kolonia Zawada (PL); Dariusz Smoleń, Jasło (PL); Wojciech Święszkowski, Warsaw (PL); Krzysztof Kurzydłowski, Warsaw (PL)

(73) Assignee: INSTYTUT WYSOKICH CISNIEN POLSKIEJ AKADEMII NAUK, Warsaw (PL)

( * ) Notice: Subject to any disclaimer, the term of this patent is extended or adjusted under 35 U.S.C. 154(b) by 34 days.

(21) Appl. No.: 14/411,881

(22) PCT Filed: Jun. 27, 2013

(86) PCT No.: PCT/PL2013/050014
§ 371 (c)(1),
(2) Date: Dec. 29, 2014

(87) PCT Pub. No.: WO2014/003588
PCT Pub. Date: Jan. 3, 2014

(65) Prior Publication Data
US 2015/0148911 A1 May 28, 2015

(30) Foreign Application Priority Data

Jun. 27, 2012 (PL) .......................... 399701

(51) Int. Cl.
*A61F 2/28* (2006.01)
*A61L 27/12* (2006.01)
(Continued)

(52) U.S. Cl.
CPC ............... *A61F 2/28* (2013.01); *A61L 27/12* (2013.01); *C04B 35/447* (2013.01);
(Continued)

(58) Field of Classification Search
None
See application file for complete search history.

(56) References Cited

U.S. PATENT DOCUMENTS

| | | | |
|---|---|---|---|
| 6,395,214 B1 | 5/2002 | Kear | |
| 2005/0031704 A1* | 2/2005 | Ahn | ....................... A61K 33/42 424/602 |

FOREIGN PATENT DOCUMENTS

WO   WO 2006/048198 A1   5/2006

OTHER PUBLICATIONS

Shi et al. ("High-Pressure and—Temperature Sintering of Nanosized Hydroxyapatite Powders", Key Engineering Materials, Trans Tech Publications Ltd., Stafa-Zurich, CH, vol. 288-289, Apr. 1, 2005, pp. 175-178) XP008058155, ISSN: 1013-9826.*

(Continued)

*Primary Examiner* — David H Willse
*Assistant Examiner* — Javier Blanco
(74) *Attorney, Agent, or Firm* — Horst M. Kasper

(57) ABSTRACT

To manufacture the implant a nanopowder of synthetic hydroxyapatite (Hap) is used having a hexagonal structure, average grain size in a range from 3 to 30 nm and the specific surface area greater than 200 m$^2$/g. First the nanopowder is formed to the desired geometric shape, and then the shape is fixed. In the step of shape information the dried nanopowder is pressed in the mold under the pressure ranging from 50 Mpa to 2 GPa. In the step of fixing the pressed nanopowder at room temperature is subjected to the pressure rising from the ambient value to the peak value selected from a range of 1 to 8 GPa and to a temperature selected from a range of (Continued)

100° C. to 600° C. for a period of time selected from a range from 30 seconds to 5 minutes. The density of thus produced implant, determined by helium method, is not less than 75% of the theoretical density.

3 Claims, 1 Drawing Sheet

(51) Int. Cl.
C04B 35/645 (2006.01)
C04B 35/447 (2006.01)
C04B 35/626 (2006.01)

(52) U.S. Cl.
CPC ...... C04B 35/62655 (2013.01); C04B 35/645 (2013.01); A61F 2310/00293 (2013.01); A61L 2400/12 (2013.01); C04B 2235/3212 (2013.01); C04B 2235/5409 (2013.01); C04B 2235/5445 (2013.01); C04B 2235/604 (2013.01); C04B 2235/6562 (2013.01); C04B 2235/6567 (2013.01); C04B 2235/662 (2013.01); C04B 2235/767 (2013.01); C04B 2235/77 (2013.01); C04B 2235/781 (2013.01); C04B 2235/96 (2013.01)

(56) References Cited

OTHER PUBLICATIONS

Shi J et al: "High-Pressure and—Temperature Sintering of Nanosized Hudroxyapatite Powders", Key Engineering Materials, Trans Tech Publications Ltd., Stafa-Zurich,CH vol. 288-289, Apr. 1, 2005 (Apr. 1, 2005) pp. 175-178 XP008058155, ISSN: 1013-9826.

* cited by examiner

METHOD FOR MANUFACTURING BONE IMPLANTS AND BONE IMPLANT

TECHNICAL FIELD

The invention relates to a method of manufacturing bone implants from powdered hydroxyapatite for use in regenerative implantology and a bone implant for such applications. As used herein, the term "implant" includes both the actual implant for direct implantation into the body, and a hydroxyapatite prefabricate in a constant form that can be used for such implant preparation.

BACKGROUND ART

There is a high demand worldwide for materials that make it possible to regenerate the bone loss which cannot be self-regenerated by the human body. The human bone in 75% of its weight consists of nonorganic substance called bioapatite, which gives the stiffness to the bone and its resistance to mechanic injuries. The use of apatite from human bone material in a bigger scale meets a psychological barrier and carries the risk of transferring the donors' pathogens to the receiver. Therefore, for many years trials have been made to produce synthetic hydroxyapatite having a composition according to the formula $Ca_{10}(PO_4)_6(OH)_2$ and being an exact equivalent of bioapatite.

A key criterion decisive for the suitability of the material for implementology is the choice of method for consolidating the powder material in the final implant, which—on the one hand—should ensure the preservation of unique properties of powdered hydroxyapatite, such as: the grain size, phase composition and morphology, and at the same time make it possible to obtain the fittings having specific geometry and mechanical strength.

There are a lot of known methods for producing medical implants using mineral powders having a desired shape, strength, structure and content of physiologically active substances, which determine the acceleration or deceleration of biodegradation or resorption processes. Commonly the fixation of the suitable shape formed from powdered materials is based on the chemical binding of powders in a form of liquid cements solidifying under the influence of chemical or physiological factors. Such processes can be used both inside the body and at the stage of initial preparation of needed fittings. Another known solution is the solidification of the powder being a component of the slurry or paste, comprising an organic, natural or synthetic polymeric substance or prepolymer, which can also be hardened inside or outside the body. For the production of fittings for implantation in the body also conventional ceramic processes are used, comprising formation of a shape by casting or pressing and subsequent sintering of the formed fitting at a high temperature. Of course, such preparation of the implants is possible only outside the body.

The International Patent Publication Number WO 2005/074453 discloses the use of a paste containing calcium phosphates, other compounds containing calcium, phosphoric acid and other ingredients, to fill bone defects (especially for internal use) which hardens rapidly after application with the secretion of hydroxyapatite. A similar solution for a filling in a liquid form, solidifying in a presence of calcium sulfate hemihydrate, is disclosed in International Patent Publication WO 87/05521. In U.S. Pat. No. 7,258,735 circa forty inorganic substances suitable for solidification of this type of cement are disclosed.

U.S. Pat. No. 5,626,861 discloses a method for preparation of bone implants from a mixture of hydroxyapatite and polymers, and optionally additives of rinsable blowing agents in the form of an emulsion in a non-aqueous solution. The fittings obtained from the mixture are mechanically and structurally close to the natural bone.

In the embodiment disclosed in U.S. 2005/209704 the mineral material, for instance hydroxyapatite, in the form of granules is coated with a polymeric layer and by melting of the polymer layer and forming of the fittings biocompatible and biodegradable implants are produced.

U.S. Pat. No. 4,097,935 discloses a process for the production of fittings from hydroxyapatite which comprises the formation of hydroxyapatite, having a grain size from 0.2 to 3 microns (with possible additions of binding agents), into a particular shape and sintering at a temperature up to 1250° C. The effect of this process is a semitransparent ceramic material with a possible admixture of other phases of calcium phosphates.

U.S. Pat. No. 5,549,123 discloses the use of self-combustible agents whose function is to form a high temperature for sintering of the prepared fitting while sustaining inside the preferred porosity.

From PL 186129 is known a bioceramic implant made of a mixture comprising hydroxyapatite with other ingredients, inter alia: sulfur, soot and aluminum oxide, formed by molding at a temperature up to 200° C., casting, pressing or extrusion.

A technology is also known of consolidation of hydroxyapatite (HAp) as a nano-powder using isostatic pressing carried out at ambient temperature and a pressure of 4 kbar, which makes it possible to receive fittings having compressive strength up to 50 MPa without the structure and geometry of the material's grains change, characterized by the Young's modulus in a range from 0.8 to 2.2 GPa and a material density of 1.9 g/cm$^3$ (D. Tadic, M. Epple, *Biomaterials*, 24 (2003), 4565-4571). However, it is known that the high temperature of isostatic pressing results in a phase transition of hydroxyapatite into calcium phosphate β (M A Auger et al. *Ceramics International*, 35 (2009), 2373-2380). A high-pressure, plasma spark sintering carried out at pressures up to 500 MPa and temperatures up to 1000° C. makes it possible obtain a transparent ceramics having a density up to 80% of the theoretical density and stable phase composition (M. Eriksson et al., *Journal of the European Ceramic Society*, 31 (2011), 1533-1540). Sintering of the powder by means of microwave energy at temperatures up to 1300° C. and a pressure of 200 MPa makes it possible to obtain a material of a 96-98% density, unchanged phase composition and grain size increased to 2.1 μm (S. Ramesh et al. *Ceramics International*, 33 (2007), 1363-1367).

A disadvantage of the known methods for HAp implants forming is the increase of the grain size and change in the phase composition of mineral material consolidated both by the reaction of cementation as well as the high temperature sintering. Limiting of the parameters of the known sintering processes in order to limit the growth effect of the particle size causes a low mechanical strength of fittings obtained with the density much lower than the theoretical density of the material.

In the production process of ceramic bone implants, having a degree of resorption adapted to osteogenic processes of the human body, it is preferred that the specific chemical composition and microstructure of the nanocrystalline HAp used for implants should not be altered during the process of consolidation (Meger J L et al. *Inorganic Chemistry*, 21 (1982), 3029-35; Dingreville R. et al., *Journal* of *Physical Mechanical Solids*, 53 (2005), 1827-1854). This condition is met when composites with polymeric compounds are used, however, in many applications, especially when exposed to mechanical stress, the resistance of composites of this type proves to be inadequate, because of their low mechanical strength and high biodegradability. Furthermore, the processes associated with the degradation of such structures often lead to severe inflammation.

DISCLOSURE OF INVENTION

The aim of the invention was to obtain pure, single-phase, nanostructural HAp fittings with a high mechanical strength required for applications in bone regenerative implantology.

This objective is to be achieved by the method implemented in the invention comprising a step of formation a HAp powder into a desired geometric shape and a step of fixing the formed shape. The method according to the invention is characterized by the use of a synthetic hydroxyapatite nanopowder with a hexagonal structure, with average grain size in a range from 3 to 30 nm and a with specific surface area greater than 200 m²/g. During the step of formation the nanopowder is dried at a temperature not exceeding 300° C. for at least one minute and then the dried nanopowder is pressed in the mold into a desired geometric shape at a pressure in the range from 50 MPa to 2 GPa. In the step of fixing the pressed nanopowder at room temperature is subjected to a pressure rising from the ambient to the peak value selected from a range from 1 to 8 GPa and to a temperature chosen from a range of 100° C. to 600° C. for a period of time selected from a range from 30 seconds to 5 minutes.

In one of the invention embodiments, in the step of fixing the pressed nanopowder is first subjected to an increasing pressure, and next the desired peak value of the pressure is maintained, the nanopowder is heated to the given temperature and maintained at that temperature for a selected time period.

In another embodiment of the invention, in the step of fixing the pressed nanopowder is heated to a selected temperature during the pressure rise. Then, while maintaining the desired peak pressure, the heated pressed nanopowder is maintained at the selected temperature for a selected period of time.

In yet another embodiment of the invention the rate of pressure rise during the step of fixing of the formed shape is at least 5 MPa per second.

In another embodiment of the invention the rate of temperature rise in the step of fixing of the formed shape is at least 1° C. per second.

The bone implant according to the invention is characterized by a density, designated using helium method, not less than 75% of the theoretical density. The average size of material's grain forming the implant, determined according to the PN-EN standard, is not larger than 50 nm, the nanohardness of this material, measured using a Berkovich indenter and a load of 4 mN, is not less than 3 GPa, and the solubility determined in accordance with ISO 10993-4 norm is from 5 to 35 mg/dm³.

The implant featured in the invention can be prepared using the above methods according to the invention.

BRIEF DESCRIPTION OF DRAWINGS

The invention has been illustrated in the accompanying drawings, in which.

MODE FOR CARRYING OUT INVENTION

The invention will be further detailed in three exemplary embodiments presented below:

Example 1

In order to form the future shape of the implant hydroxyapatite powder with a grain size in a range of 3 to 30 nm was dried for two hours in a vacuum oven at 200° C. and subjected to a pressure of 0.5 atmospheres, afterwards the dried powder was cooled to room temperature under argon at a pressure of 1 atm. Then, 130 mg of such dried hydroxyapatite was weighed and placed in a steel mold with a diameter of 5 mm, in which it was compressed in a known manner, under a vacuum and a pressure of 150 MPa maintained for 30 seconds. In order to consolidate the shape of the resulting pressed hydoroxyapatite ("molding") in the form of a cylinder with a diameter of 5 mm, the molding was placed in a ceramic frame acting as a pressure medium.

Between the molding and ceramic frame a graphite heater was placed with an internal diameter of 5 mm, 1V voltage supply and power adjustable from 200 to 1000 W, making it possible to heat the hydroxyapatite. All this was closed using spacers made of boron nitride. The prepared molding was placed in a press equipped with a toroidal anvil and subjected to a pressure increasing for 20 minutes from ambient value to the peak value of 7 GPa, and then it was kept under the pressure achieved. After 5 minutes the heater was switched off, which after 30 seconds resulted in a drop of hydroxyapatite molding temperature to 230° C. and this temperature was then maintained for 3 minutes. The fixing step of the implant's shape was ended with the reduction of operating pressure and temperature to the room values.

As a result of the described above process a cylinder of hydroxyapatite was obtained having a uniform structure, which according to x-ray diffraction has not changed its phase composition relative to the initial material.

Figure 1:
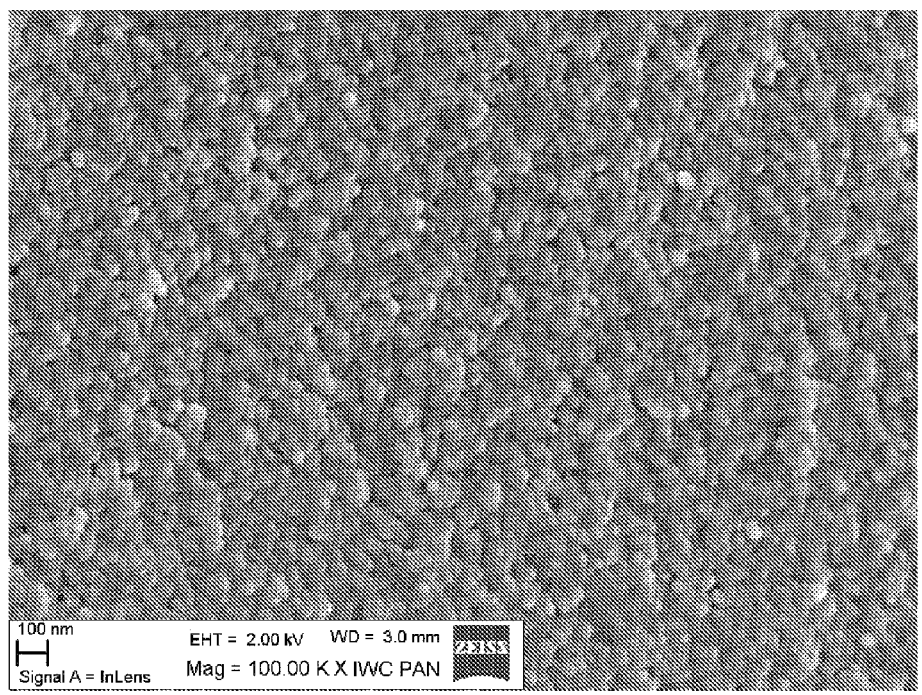
FIG. 1 shows an SEM image of the implant obtained from nanopowder HAp with the average size of grains less than 30 nm, produced by the method according to the invention as described in Example 1.
Figure 2:
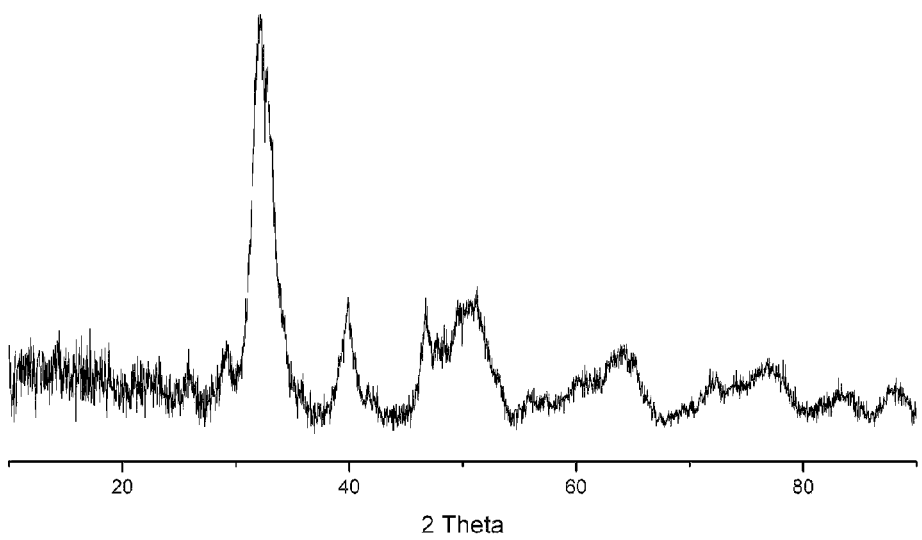
FIG. 2 shows the XRD diffraction graph of this implant's material.

The microhardness of the implant obtained measured by Vickers method with a load of 0.2 kg at the time of 15 seconds was 417 HV0.2, the nanohardness measured using a Berkovich indenter and the 4 mN load was 8.3 GPa, and Young's modulus—124 GPa. A morphological analysis performed by means of scanning electron microscopy (SEM image of the sample is shown in FIG. 1) showed a uniform structure of the material having the average grain size, determined by the PN-EN standard, of no more than 50 nm. The density of the resulting implant material, measured with a helium pycnometer, was 2.62 g/cm³.

Example 2

The molding of powdered hydroxyapatite was prepared similarly as in Example 1, but the drying process was carried out at 190° C.

The step of shape fixing was carried out under the same conditions as in Example 1 but the pressure peak value was 4 GPa, and the heating was carried out at a temperature of 200° C. In this case also the material obtained had the same phase composition as the initial hydroxyapatite, but the microhardness of the resulting implant measured as described in Example 1 was 333 HV0.2. The density of the resulting implant material, measured with a helium pycnometer, was 2.62 g/cm³.

Example 3

A cylindrical implant made of hydroxyapatite was prepared as described in Example 2, but the peak value of pressure during the step of shape fixing was 8 MPa, and the temperature of annealing was 500° C. As before, the material obtained had a constant structure phase with respect to that of the initial material and was characterized by the Young's modulus of 83 GPa, and—measured as described in Example 1—microhardness of 500 HV0.2 and nanohardness of 3.5 GPa. The density of the resulting implant material, measured with a helium pycnometer, was 2.62 g/cm3.

Using the methods described above from hydroxyapatite powder both ready for use implants can be made (such as bone screws or nails) as well as universal moldings, which in the given specific case of bone damage, even during operation, can be adjusted mechanically for the best fit. The heating to a given temperature required to consolidate the shape of the molding may be also carried out during the phase of pressure increase to which we molding is subjected.

The invention claimed is:

1. A bone implant consisting of pure, single-phase, nanostructural hydroxyapatite (HAp), characterized in that its density, determined by helium method, is not less than 75% of the theoretical density, the average grain size of the material forming the implant, determined on the basis of the PN-EN standard, is not larger than 50 nm, the nanohardness of this material, measured by Berkovich indenter using a load of 4 mN, is not less than 3 GPa, and its solubility, determined according to ISO 10993-4 norm, is from 5 to 35 mg/dm³,
   wherein said bone implant is manufactured using a nanopowder of synthetic hydroxyapatite (HAp) having a hexagonal structure, an average grain size in a range from 3 nm to 30 nm, and a specific surface area greater than 200 m²/g,
   wherein said bone implant is manufactured by a method comprising a step of shape formation of said nanopowder of synthetic hydroxyapatite (HAp) into a desired geometric shape, and subsequently a step of fixing the formed shape,
   wherein in the step of shape formation, the nanopowder of synthetic hydroxyapatite (HAp) is dried at a temperature not exceeding 300° C. for at least one minute and then the dried nanopowder is pressed in a mold into a desired geometric shape at a pressure in the range from 50 MPa to 2 GPa, and
   wherein in the step of fixing, the pressed nanopowder is at room temperature and is subjected to a pressure rising from the ambient value to a peak value selected from a range from 1 GPa to 8 GPa and to a temperature chosen from a range of 100° C. to 600° C. for a period of time selected from a range from 30 seconds to 5 minutes.

2. The bone implant according to claim 1, wherein the implant is placed in a steel mold with a diameter of 5 mm, in which it was compressed under a vacuum and a pressure of 150 Mpa maintained for 30 seconds.

3. The bone implant according to claim 1, wherein the rate of pressure rise in the step of fixing is at least 5 MPa per second.

* * * * *